US011553828B2

(12) United States Patent
Kono et al.

(10) Patent No.: US 11,553,828 B2
(45) Date of Patent: Jan. 17, 2023

(54) DIAGNOSIS SUPPORT APPARATUS, DIAGNOSIS SUPPORT METHOD AND COMPUTER-READABLE NON-TRANSITORY STORAGE MEDIUM FOR STORING PROGRAM

(71) Applicant: OLYMPUS CORPORATION, Tokyo (JP)

(72) Inventors: Takashi Kono, Hachioji (JP); Makoto Kitamura, Hachioji (JP); Hirokazu Godo, Hachioji (JP); Toshiya Kamiyama, Tama (JP); Katsuyoshi Taniguchi, Hino (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 516 days.

(21) Appl. No.: 16/745,487

(22) Filed: Jan. 17, 2020

(65) Prior Publication Data

US 2020/0146529 A1 May 14, 2020

Related U.S. Application Data

(63) Continuation of application No. PCT/JP2017/026233, filed on Jul. 20, 2017.

(51) Int. Cl.
*A61B 1/00* (2006.01)
*A61B 1/06* (2006.01)
*G06K 9/62* (2022.01)

(52) U.S. Cl.
CPC ...... *A61B 1/000094* (2022.02); *A61B 1/0638* (2013.01); *A61B 1/0684* (2013.01); *G06K 9/628* (2013.01)

(58) Field of Classification Search
CPC . G06T 2207/10068; G06T 2207/30096; G06T 7/0012; G06T 2207/20084;
(Continued)

(56) References Cited

U.S. PATENT DOCUMENTS

2010/0182412 A1* 7/2010 Taniguchi ............ G16H 10/60
345/473
2011/0301443 A1* 12/2011 Yamaguchi .......... A61B 1/0655
600/324
(Continued)

FOREIGN PATENT DOCUMENTS

JP 2001-104253 A 4/2001
JP 2010-172673 A 8/2010
(Continued)

OTHER PUBLICATIONS

International Search Report dated Sep. 19, 2017 issued in PCT/JP2017/026233.

*Primary Examiner* — Alex Kok S Liew
(74) *Attorney, Agent, or Firm* — Scully, Scott, Murphy & Presser, P.C.

(57) ABSTRACT

A diagnosis support apparatus performs identification for a plurality of support items, which are identification classifications about diagnosis support, and the diagnosis support apparatus is provided with a processor. The processor performs analysis processing for acquiring analysis results including an analysis result about an observation mode by analyzing at least one of an input signal specifying the observation mode and an observation image obtained by observing an inside of a subject with an endoscope; performs support item setting processing for setting a support item corresponding to the analysis results obtained by the analysis processing, among the plurality of support items, which are the identification classifications; and generates diagnosis support information, which is information used for (Continued)

diagnosis of a legion candidate area included in the observation image, based on an identification index corresponding to the set support item and the observation image.

12 Claims, 8 Drawing Sheets

(58) Field of Classification Search
CPC . G06T 2207/20081; G06T 2207/10024; G06T 7/0016; G06T 2207/10016; G06T 2200/24; G06T 2207/30092; G06T 7/0014; G06T 2207/30028; G06T 2207/30101; G06T 7/11; G06T 2207/30004; G06T 7/70; G06T 2207/30032; G06T 2207/10152; G06T 11/60; G06T 2207/10081; G06T 2207/10088; G06T 5/50; G06T 1/00; G16H 30/20; G16H 10/60; G16H 30/40; G16H 50/20

See application file for complete search history.

(56) References Cited

U.S. PATENT DOCUMENTS

| | | | |
|---|---|---|---|
| 2015/0366444 | A1 | 12/2015 | Morimoto et al. |
| 2016/0183774 | A1* | 6/2016 | Shiraishi .......... A61B 1/000094 |
| | | | 600/328 |

FOREIGN PATENT DOCUMENTS

| | | |
|---|---|---|
| JP | 2011-212094 A | 10/2011 |
| JP | 2016-007354 A | 1/2016 |
| JP | 2016-021248 A | 2/2016 |

* cited by examiner

FIG. 3

| SUPPORT ITEM | ANALYSIS RESULT | WHITE LIGHT OBSERVATION | SPECIAL LIGHT OBSERVATION + UNENLARGED | SPECIAL LIGHT OBSERVATION + UNENLARGED + TUMOR | SPECIAL LIGHT OBSERVATION + ENLARGED | SPECIAL LIGHT OBSERVATION + ENLARGED + TUMOR | WHITE LIGHT OBSERVATION + DYE SPRAYING |
|---|---|---|---|---|---|---|---|
| IMAGE-PICKED-UP SITE INFORMATION | | ○ | | | | | |
| SIZE INFORMATION | | ○ | | | | | |
| MACROSCOPIC CLASSIFICATION | | ○ | | | | | |
| NICE CLASSIFICATION | LIKELIHOOD OF EACH CLASS | | ○ | | | | |
| NICE CLASSIFICATION | LIKELIHOOD OF EACH CLASS + INTER-CLASS AREA RATIO | | | ○ | | | |
| JNET CLASSIFICATION | LIKELIHOOD OF EACH CLASS | | | | ○ | | |
| JNET CLASSIFICATION | LIKELIHOOD OF EACH CLASS + INTER-CLASS AREA RATIO | | | | | ○ | |
| PIT PATTERN CLASSIFICATION | LIKELIHOOD OF EACH CLASS | | | | | | ○ |

TA

DIAGNOSIS SUPPORT APPARATUS, DIAGNOSIS SUPPORT METHOD AND COMPUTER-READABLE NON-TRANSITORY STORAGE MEDIUM FOR STORING PROGRAM

CROSS REFERENCE TO RELATED APPLICATION

This application is a continuation application of PCT/JP2017/026233 filed on Jul. 20, 2017, the entire contents of which are incorporated herein by this reference.

BACKGROUND OF THE INVENTION

1. Field of the Invention

The present invention relates to a diagnosis support apparatus, a diagnosis support method and a computer-readable non-transitory storage medium in which a program is stored, and in particular to a diagnosis support apparatus for presenting diagnosis support information during endoscopic observation, a diagnosis support method and a computer-readable non-transitory storage medium for storing a program.

2. Description of the Related Art

For endoscopic observation in a medical field, computer-aided diagnosis (CAD) technology is known as technology to present information to support diagnosis to a doctor and the like for a lesion existing in a picked-up image of biological tissue. In Japanese Patent Application Laid-Open Publication No. 2001-104253 (hereinafter referred to as Patent Literature 1) and Japanese Patent Application Laid-Open Publication No. 2011-212094 (hereinafter referred to as Patent Literature 2), techniques related to CAD are proposed.

Patent Literature 1 discloses a technique for, in a system provided with a plurality of CAD apparatuses, selecting a CAD apparatus suitable for interpretation request information inputted by a user from among the plurality of CAD apparatuses and presenting a diagnosis support result by the selected CAD apparatus.

Patent Literature 2 discloses a technique for, in a system provided with a plurality of legion extracting portions capable of extracting a plurality of different kinds of legions, respectively, acquiring diagnosis information based on patient information, selecting a suitable legion extracting portion from among the plurality of legion extracting portions according to a result of judgment about whether there is definitive diagnosis in the diagnosis information and displaying a legion extracted by the selected legion extracting portion.

SUMMARY OF THE INVENTION

A diagnosis support apparatus of an aspect of the present invention performs identification for a plurality of support items, which are identification classifications about diagnosis support, and the diagnosis support apparatus includes a processor. The processor performs analysis processing for acquiring analysis results including an analysis result about an observation mode by analyzing at least one of an input signal specifying the observation mode and an observation image obtained by observing an inside of a subject with an endoscope; performs support item setting processing for setting a support item corresponding to the analysis results obtained by the analysis processing, among the plurality of support items, which are the identification classifications; and generates diagnosis support information, which is information used for diagnosis of a legion candidate area included in the observation image, based on an identification index corresponding to the set support item and the observation image.

A diagnosis support method of an aspect of the present invention is a diagnosis support method for performing identification for a plurality of support items, which are identification classifications about diagnosis support, the diagnosis support method including: performing analysis processing for acquiring analysis results including an analysis result about an observation mode by analyzing at least one of an input signal specifying the observation mode and an observation image obtained by observing an inside of a subject with an endoscope; setting a support item corresponding to the analysis results obtained by the analysis processing, among the plurality of support items, which are the identification classifications; and generating diagnosis support information, which is information used for diagnosis of a legion candidate area included in the observation image, based on an identification index corresponding to the set support item and the observation image.

A storage medium of an aspect of the present invention is a computer-readable non-transitory storage medium in which a program for performing identification for a plurality of support items which are identification classifications about diagnosis support is stored, wherein the program causes a computer to execute a procedure of: acquiring analysis results including an analysis result about an observation mode by analyzing at least one of an input signal specifying the observation mode and an observation image obtained by observing an inside of a subject with an endoscope; setting a support item corresponding to the analysis results among the plurality of support items, which are the identification classifications; and generating diagnosis support information, which is information used for diagnosis of a legion candidate area included in the observation image, based on an identification index corresponding to the set support item and the observation image.

BRIEF DESCRIPTION OF THE DRAWINGS

FIG. 3 is a diagram showing an example of a table referred to when the process shown in FIGS. 2A and 2B is performed;

DETAILED DESCRIPTION OF THE PREFERRED EMBODIMENT(S)

An embodiment of the present invention will be described below with reference to drawings.

Figure 1:
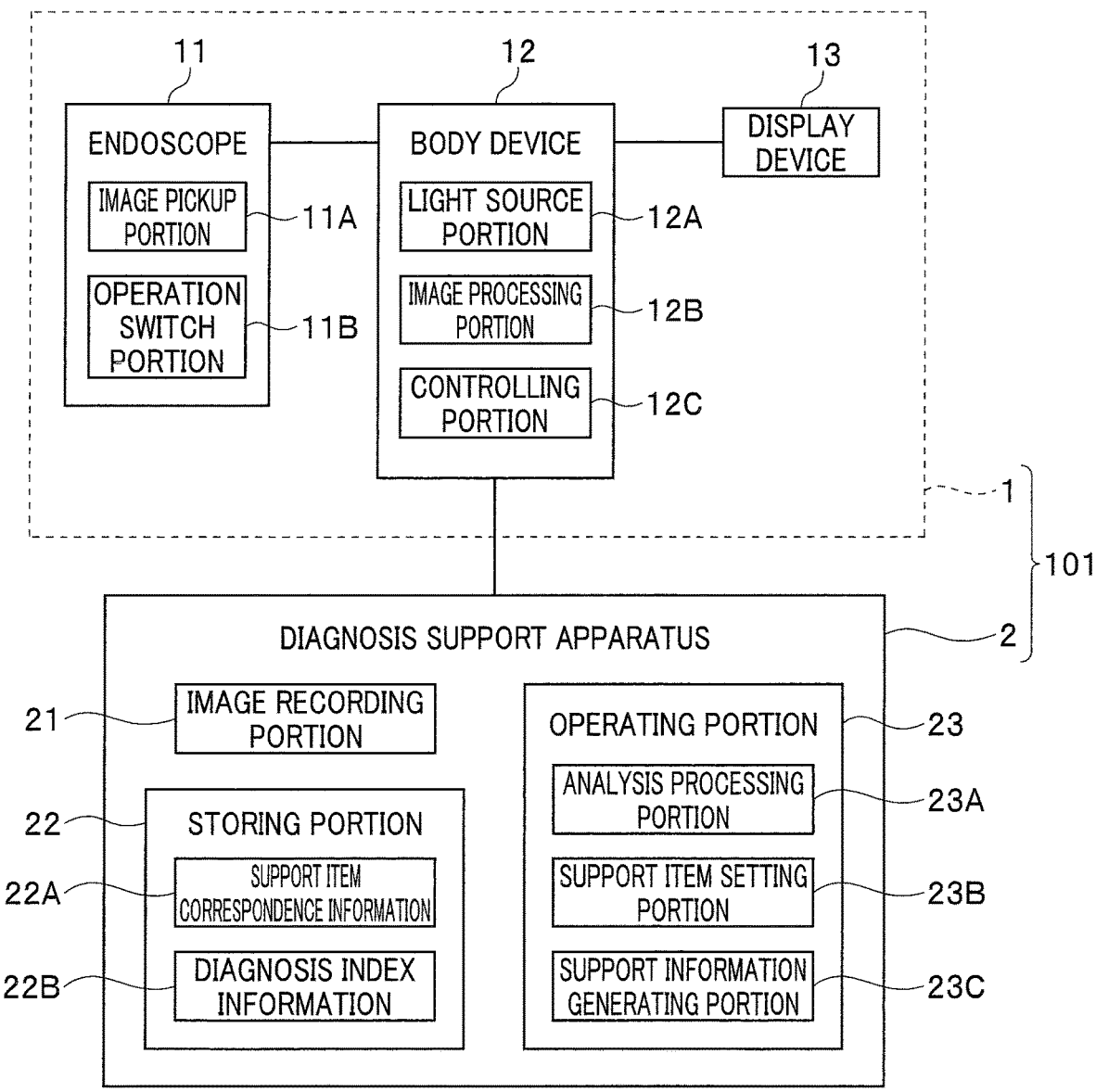
FIG. 1 is a diagram showing a configuration of a main part of a medical system including a diagnosis support apparatus according to an embodiment.

For example, as shown in FIG. 1, a medical system 101 is configured including an endoscope system 1 and a diagnosis support apparatus 2. FIG. 1 is a diagram showing a configuration of a main part of a medical system including a diagnosis support apparatus according to the embodiment.

The endoscope system 1 is configured to be capable of picking up an image of an object such as biological tissue existing in a subject (in a living body) to acquire an observation image and generating a display image corresponding to the acquired observation image to display the display image. As shown in FIG. 1, the endoscope system 1 is configured including an endoscope 11, a body device 12 and a display device 13.

The endoscope 11 is configured, for example, being provided with an insertion portion (not shown) in an elongated shape that is insertable into a subject and an operation portion (not shown) provided on a proximal end portion of the insertion portion. Further, the endoscope 11 is configured to be detachably connected to the body device 12, for example, via a universal cable (not shown) extending from the operation portion. Inside the endoscope 11, for example, a light guiding member (not shown) such as an optical fiber for guiding illumination light supplied from the body device 12 and emitting the illumination light from a distal end portion of the insertion portion is provided. Further, the endoscope 11 is configured including an image pickup portion 11A provided on the distal end portion of the insertion portion and an operation switch portion 11B provided on the operation portion.

The image pickup portion 11A is configured, for example, being provided with a CCD image sensor or a CMOS image sensor. The image pickup portion 11A is configured to pick up an image of return light from an object illuminated by illumination light emitted via the distal end portion of the insertion portion, generate an image pickup signal corresponding to the return light the image of which has been picked up and output the image pickup signal to the body device 12.

The operation switch portion 11B is configured being provided with one or more switches capable of giving an instruction corresponding to an operation by a user to the body device 12. More specifically, the operation switch portion 11B is provided, for example, with an observation mode setting switch which is a switch capable of giving an instruction to set an observation mode of the endoscope system 1 to either white light observation or special light observation, and an electronic zoom switch which is a switch capable of giving an instruction to set a magnification for electronic magnification changing processing performed in the body device 12.

The body device 12 is configured to be detachably connected to each of the diagnosis support apparatus 2, the endoscope 11 and the display device 13. For example, as shown in FIG. 1, the body device 12 is configured including a light source portion 12A, an image processing portion 12B and a controlling portion 12C.

The light source portion 12A is configured, for example, being provided with one or more light emitting devices. The light source portion 12A is configured to be capable of generating illumination light corresponding to control of the controlling portion 12C and supplying the illumination light to the endoscope 11. More specifically, the light source portion 12A is configured to be capable of generating, for example, white light which is broadband light including blue light, green light and red light according to control of the controlling portion 12C and supplying the generated white light to the endoscope 11 as illumination light. Further, the light source portion 12A is configured to be capable of generating, for example, special light that includes narrowband blue light the center wavelength of which is set to around 415 nm and narrowband green light the center wavelength of which is set to around 540 nm according to control of the controlling portion 12C and supplying the generated special light to the endoscope 11 as illumination light.

The image processing portion 12B is configured, for example, being provided with an image processing circuit. The image processing portion 12B is configured to be capable of generating an observation image based on an image pickup signal outputted from the endoscope 11, performing image processing corresponding to control of the controlling portion 12C, for the generated observation image, and outputting the image-processed observation image to the display device 13 as a display image. More specifically, the image processing portion 12B is configured to perform, for example, magnification changing processing for performing enlargement or reduction with a magnification corresponding to control of the controlling portion 12C, for an observation image, and processing for adding a character string showing the magnification in the observation image, as the image processing described above. Further, the image processing portion 12B is configured to sequentially output observation images for which the above image processing has been performed, to the diagnosis support apparatus 2. Further, the image processing portion 12B is configured to be capable of, according to control of the controlling portion 12C, generating a display image, which is an observation image to which diagnosis support information outputted from the diagnosis support apparatus 2 is added, and outputting the display image to the display device 13.

The controlling portion 12C is configured, for example, being provided with a control circuit. The controlling portion 12C is configured to control the light source portion 12A to generate illumination light corresponding to an observation mode set by the observation mode setting switch of the operation switch portion 11B. The controlling portion 12C is configured to control the image processing portion 12B to perform the magnification changing processing with a magnification set by the electronic zoom switch of the operation switch portion 11B. Further, the controlling portion 12C is configured to control the image processing portion 12B to add diagnosis support information outputted from the diagnosis support apparatus 2 to an observation image.

Note that, in the present embodiment, the image processing portion 12B and the controlling portion 12C of the body device 12 may be configured as individual electronic circuits, or may be configured as circuit blocks in an integrated circuit such as an FPGA (field programmable gate array). In the present embodiment, for example, the body device 12 may be configured being provided with one or more CPUs.

The diagnosis support apparatus 2 is configured, for example, being provided with a computer. The diagnosis support apparatus 2 is configured to be detachably connected to the body device 12. The diagnosis support apparatus 2 is configured to generate diagnosis support information based on an observation image outputted from the body device 12 and output the generated diagnosis support information to the body device 12. Further, for example, as shown in FIG. 1, the diagnosis support apparatus 2 is configured including an image recording portion 21, a storing portion 22 and an operating portion 23.

The image recording portion 21 is configured, for example, being provided with an image recording circuit. The image recording portion 21 is configured to record observation images sequentially outputted from the body device 12.

The storing portion 22 is configured, for example, being provided with a storage circuit such as a ROM. The storing portion 22 is configured to be capable of storing analysis results, image-picked-up site information and the like obtained by an analysis processing portion 23A described later. Further, in the storing portion 22, information used for generation of diagnosis support information by the operating portion 23 is stored. More specifically, for example, support item correspondence information 22A and diagnosis index information 22B are stored in the storing portion 22.

The support item correspondence information 22A is configured being provided with one or more tables showing correspondence relationships between analysis results of an observation image by the operating portion 23 and support items which are identification classifications set when diagnosis support information is generated by the operating portion 23. Note that a specific example of the tables included in the support item correspondence information 22A will be described later.

The diagnosis index information 22B is configured being provided with various indexes for obtaining information corresponding to the support items in the support item correspondence information 22A (identification indexes). Note that specific examples of the indexes included in the diagnosis index information 22B will be described later.

The operating portion 23 as a processor is configured, for example, being provided with an operation circuit. For example, the operating portion 23 may be configured with a CPU, an FPGA or the like, may be such that operates according to a program stored in a memory not shown to control each portion, or may be such that realizes a part or all of functions in a hardware electronic circuit. The operating portion 23 is configured to analyze an observation image recorded to the image recording portion 21 to acquire analysis results and generate diagnosis support information corresponding to the acquired analysis results to sequentially output the diagnosis support information to the body device 12. The operating portion 23 is configured including the analysis processing portion 23A, a support item setting portion 23B and a support information generating portion 23C.

The analysis processing portion 23A is configured to perform processing for sequentially analyzing observation images recorded to the image recording portion 21 one by one to obtain analysis results. In other words, the analysis processing portion 23A is configured to analyze observation images sequentially inputted to the diagnosis support apparatus 2 during observation of an inside of a subject with the endoscope 11 and acquire the analysis results. Note that a specific example of the processing performed by the analysis processing portion 23A will be described later.

The support item setting portion 23B is configured to set a different support item according to analysis results obtained by the analysis processing portion 23A, referring to the support item correspondence information 22A stored in the storing portion 22. Further, the support item setting portion 23B is configured to, when a predetermined processing result is obtained in processing related to generation of diagnosis support information by the support information generating portion 23C, additionally set a support item corresponding to the predetermined processing result, referring to the support item correspondence information 22A stored in the storing portion 22.

The support information generating portion 23C is configured to acquire an index corresponding to a support item set by the support item setting portion 23B, by referring to the diagnosis index information 22B stored in the storing portion 22. Further, the support information generating portion 23C is configured to, based on the index acquired as described above and the same observation image that has been analyzed by the analysis processing portion 23A, perform processing for generating diagnosis support information, which is information used for diagnosis of a lesion candidate area included in the observation image, and outputting the diagnosis support information to the body device 12. Note that a specific example of the processing performed by the support information generating portion 23C will be described later.

Figure 2A:
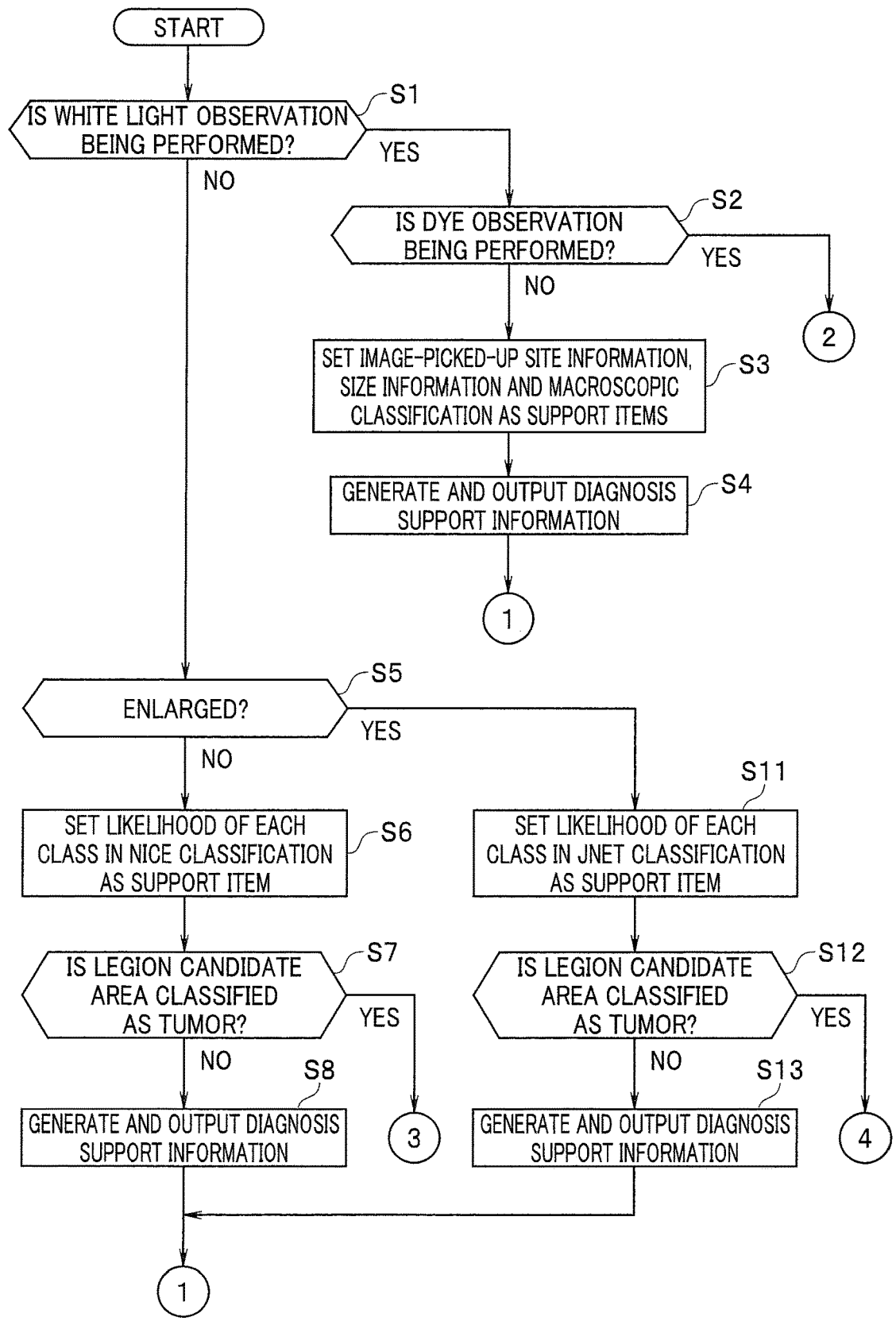
FIG. 2A is a flowchart showing a part of a specific example of a process performed in the diagnosis support apparatus according to the embodiment.
Figure 2B:
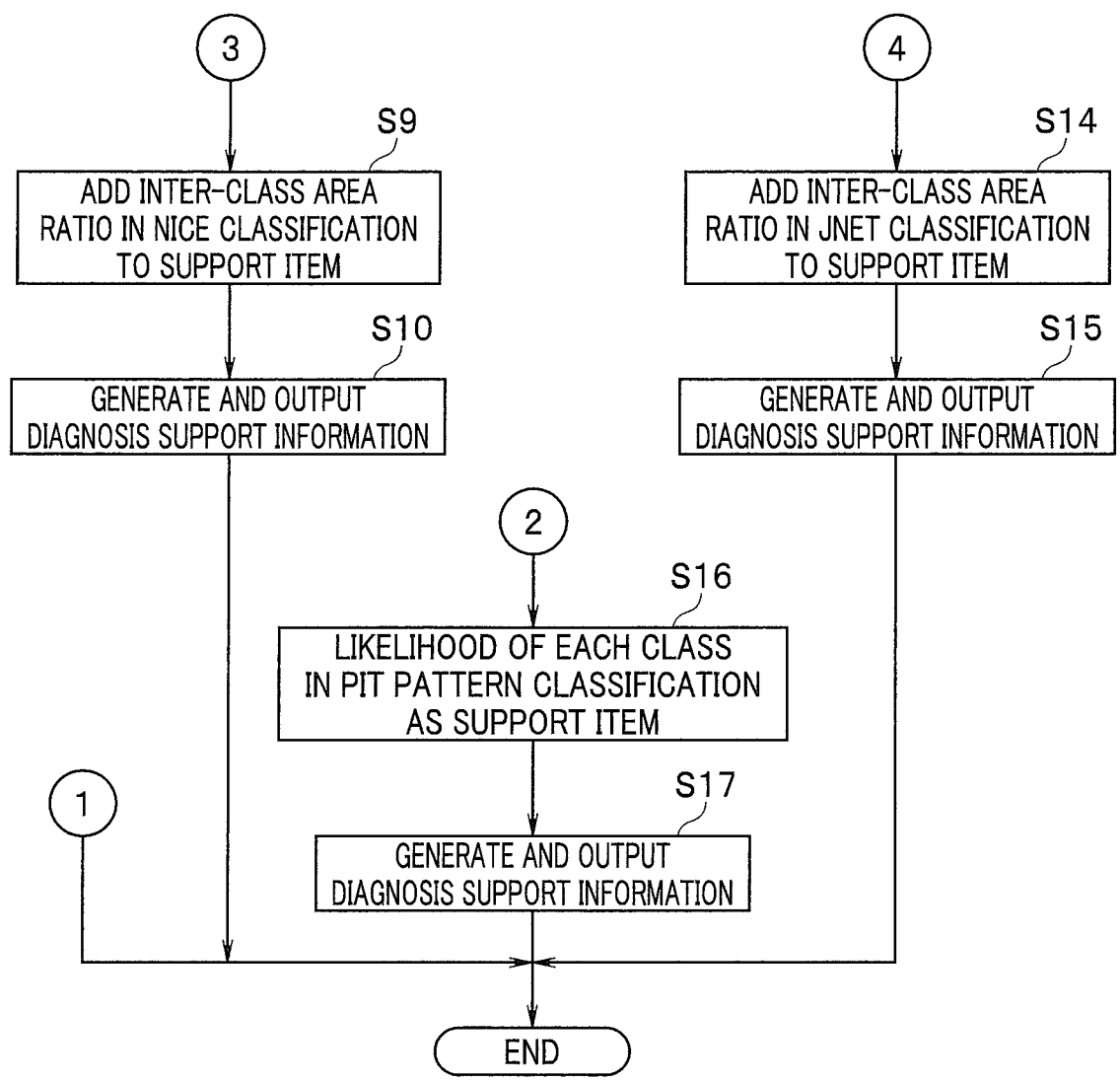
FIG. 2B is a flowchart showing a continuation of the process of FIG. 2A.

Next, operation of the present embodiment will be described with reference to FIGS. 2A and 2B. Note that description will be made below on a case where diagnosis is made on a lesion candidate area existing in a large intestine, as a representative example. FIG. 2A is a flowchart showing a part of a specific example of a process performed in the diagnosis support apparatus according to the embodiment. FIG. 2B is a flowchart showing a continuation of the process of FIG. 2A.

After connecting each portion of the endoscope system 1 and turning on a power source, the user gives an instruction to set the observation mode of the endoscope system 1 to the white light observation by operating the observation mode setting switch of the operation switch portion 11B.

When detecting that the instruction to set the observation mode of the endoscope system 1 to the white light observation has been given by the observation mode setting switch of the operation switch portion 11B, the controlling portion 12C controls the light source portion 12A to generate white light. Then, in response to such control of the controlling portion 12C, white light is supplied from the light source portion 12A to the endoscope 11; an image of return light from an object illuminated by the white light is picked up by the image pickup portion 11A; a white light observation image corresponding to an image pickup signal outputted from the image pickup portion 11A is generated by the image processing portion 12B; and the white light observation image is displayed on the display device 13 as a display image and recorded to the image recording portion 21.

After inserting the insertion portion of the endoscope 11 until the insertion portion reaches the deepest part (for example, near a cecum) in the large intestine of the examinee, the user searches for a legion candidate area in the large intestine by confirming the white light observation image displayed on the display device 13 while performing an operation for removing the insertion portion from inside the large intestine. Then, when a legion candidate area is discovered by the user, a white light observation image including the legion candidate area is generated by the image processing portion 12B, and the white light observation image is displayed on the display device 13 as a display image and recorded to the image recording portion 21.

By analyzing the color tone and the like of the observation image recorded to the image recording portion 21, the analysis processing portion 23A acquires an analysis result about whether or not the white light observation is being performed in the endoscope system 1 (step S1 in FIG. 2A). In other words, at step S1 in FIG. 2A, by analyzing the color tone and the like of the observation image recorded to the image recording portion 21, the analysis processing portion 23A acquires an analysis result about which of the white light observation and the narrowband light observation the object in the subject is being observed by.

Note that, according to the present embodiment, the analysis processing portion 23A is not limited to obtaining the analysis result about whether or not the white light observation is being performed in the endoscope system 1 by analyzing an observation image (recorded to the image recording portion 21) inputted from the body device 12 but may obtain a similar analysis result by analyzing an input signal inputted from the body device 12. More specifically, the analysis processing portion 23A may obtain, for example, when an instruction signal showing an instruction given by the observation mode setting switch of the operation switch portion 11B is inputted to the diagnosis support apparatus 2 via (the controlling portion 12C of) the body device 12, the analysis result about whether or not the white light observation is being performed in the endoscope system 1, based on the instruction signal.

Note that various kinds of input signals specifying the observation mode can be adopted for the analysis processing of the analysis processing portion 23A. For example, an instruction signal generated by an operation of specifying the white light observation, the special light observation, dye observation, enlarged observation or the like may be used as an input signal.

If obtaining an analysis result that the white light observation is being performed in the endoscope system 1 (S1: YES), the analysis processing portion 23A acquires image-picked-up site information, which is information showing a site in the subject where the legion candidate area included in the white light observation image has been image-picked up, based on the white light observation image recorded to the image recording portion 21, and stores the acquired image-picked-up site information into the storing portion 22.

Note that, in the present embodiment, the image-picked-up site information may be obtained, for example, by performing analysis using a discriminator provided with a function capable of identifying a site in the subject according to the kind of the object included in the white light observation image or by performing analysis using one or more feature values obtained from the white light observation image. Hereinafter, description will be made on a case where information showing that an image of the legion candidate area has been picked up in a large intestine is obtained as the image-picked-up site information, as a representative example.

If obtaining the analysis result that the white light observation is being performed in the endoscope system 1 (S1: YES), the analysis processing portion 23A acquires an analysis result about whether the dye observation, which is such an observation method that, in a state of dye for dyeing the legion candidate area included in the white light observation area being sprayed, observation of the legion candidate area is performed, is being performed or not, by further analyzing the color tone and the like of the same white light observation image that has been targeted by the processing of step S1 in FIG. 2A (step S2 in FIG. 2A). In other words, by analyzing the color tone and the like of the same white light observation image that has been targeted by the processing of step S1 in FIG. 2A, the analysis processing portion 23A acquires an analysis result about whether the legion candidate area included in the white light observation image is dyed or not, at step S2 in FIG. 2A.

Here, a structure with a high absorbance in a red area is not included in the white light observation image obtained during the white light observation. Therefore, a red component image obtained by performing color separation processing for the white light observation image recorded to the image recording portion 21 is an image showing a structure near to the surface of biological tissue. In comparison, for example, if crystal violet with a high absorbance is sprayed in the red area as dye for the dye observation, a structure area where steep edges are dense can occur in the red component image due to liquid dye staying in grooves on the surface of the biological tissue. Therefore, the analysis processing portion 23A of the present embodiment can acquire the analysis result about whether the dye observation is being performed or not, for example, by calculating variance Vr of pixel values of respective pixels included in the red component image obtained by performing color separation processing for the same white light observation image that has been targeted by the processing of step S1 in FIG. 2A. According to such processing, for example, an analysis result that the dye observation is being performed is acquired when the variance Vr is larger than a predetermined value TH, and an analysis result that the dye observation is not being performed is acquired when the variance Vr is equal to or smaller than the predetermined value TH.

If obtaining an analysis result that the white light observation is not being performed in the endoscope system 1, that is, an analysis result that the special light observation is being performed in the endoscope system 1 (S1: NO), the analysis processing portion 23A subsequently performs processing of step S5 in FIG. 2A described later.

If the analysis result that the white light observation is being performed in the endoscope system 1 is obtained by step S1 in FIG. 2A (S1: YES), the support item setting portion 23B sets a support item, referring to, for example, a table TA as shown in FIG. 3, the table TA corresponding to the image-picked-up site information (large intestine) obtained together with the analysis result, in the support item correspondence information 22A stored in the storing portion 22. Note that the table TA may be configured having a format different from the format as shown in FIG. 3 as far as the table TA shows correspondence relationships between the analysis results of the observation image by the analysis processing portion 23A and the support item set by the support item setting portion 23B to support diagnosis of the legion candidate area discovered in the large intestine. It is assumed that, for example, until the image-picked-up site information stored in the storing portion 22 is updated from "large intestine" to a different site, the support item setting portion 23B sets a support item, referring to the table TA irrespective of whether the white light observation is being performed in the endoscope system 1 or not. FIG. 3 is a diagram showing an example of a table referred to when the process shown in FIGS. 2A and 2B is performed.

If the analysis result that the dye observation is being performed is obtained by step S2 in FIG. 2A (S2: YES), the support item setting portion 23B subsequently performs processing of step S16 in FIG. 2B described later. If an analysis result that the dye observation is not being performed is obtained by step S2 in FIG. 2A (S2: NO), the support item setting portion 23B sets each of image-picked-up site information, size information and macroscopic classification, which are items corresponding to "white light observation" in the table TA as a support item corresponding to the analysis result obtained by step S1 in FIG. 2A, by referring to the table TA illustrated in FIG. 3 (step S3 in FIG. 2A). In other words, if an analysis result showing that the object in the subject is being observed by the white light observation is obtained at step S3 in FIG. 2A, the support item setting portion 23B sets each of a site in the subject where the legion candidate area has been image-picked up, the size of the legion candidate area, and a classification result by the macroscopic classification, which is a classification method having a plurality of classes for classifying the legion candidate area according to the shape of the legion candidate area, as a support item. Note that, according to the present embodiment, at step S3 in FIG. 2A, at least one item has to be set as a support item among the site in the subject where the legion candidate area has been image-picked up, the size of the legion candidate area, and the classification result by the classification method having the plurality of classes for classifying the legion candidate area according to the shape of the legion candidate area.

The support information generating portion 23C acquires an index corresponding to the support items set at step S3 in FIG. 2A, by referring to the diagnosis index information 22B stored in the storing portion 22.

More specifically, the support information generating portion 23C acquires, for example, as an index corresponding to the image-picked-up site information included among the support items set at step S3 in FIG. 2A, an index for identifying the site in the subject where the legion candidate area has been image-picked up, based on one or more feature values and the like obtained from the white light observation image, by referring to the diagnosis index information 22B stored in the storing portion 22. Further, the support information generating portion 23C acquires, for example, as an index corresponding to the size information included among the support items set at step S3 in FIG. 2A, an index for estimating the actual size of the legion candidate area included in the white light observation image, by referring to the diagnosis index information 22B stored in the storing portion 22. Further, the support information generating portion 23C acquires, for example, as an index corresponding to the macroscopic classification included among the support items set at step S3 in FIG. 2A, a classification index for classifying the legion candidate area included in the white light observation image obtained by image-picking up the inside of the large intestine to any one of the plurality of classes in the macroscopic classification, by referring to the diagnosis index information 22B stored in the storing portion 22.

The support information generating portion 23C generates diagnosis support information based on the indexes acquired according to the support items set at step S3 in FIG. 2A and the same white light observation image that has been targeted by the processing of step S1 in FIG. 2A, and outputs the generated diagnosis support information to the body device 12 (step S4 in FIG. 2A). According to such an operation of step S4 in FIG. 2A, for example, the diagnosis support information including information showing that the legion candidate area discovered by the user exists in the large intestine, information showing a result of estimation of the actual length of the longest diameter of the legion candidate area, and information showing a classification result obtained by classifying the legion candidate area by the macroscopic classification is generated, and the generated diagnosis support information is outputted from the diagnosis support apparatus 2 to the body device 12. Note that, in the present embodiment, for example, a method such as a judgment method by machine learning in which, with a large number of teacher images each of which is attached with tag information about a site, size and macroscopic classification used as teacher data, a judgment result is obtained by a hierarchical neural network (such as DCNN) can be used as a judgment method for judging the site, size and macroscopic classification.

Note that, when generating the diagnosis support information at step S4 in FIG. 2A, the support information generating portion 23C may use the image-picked-up site information obtained together with the analysis result by step S1 in FIG. 2A.

The controlling portion 12C controls the image processing portion 12B to add the diagnosis support information outputted from the diagnosis support apparatus 2 to the white light observation image. According to such an operation of the controlling portion 12C, a display image D1 including the white light observation image generated by the image processing portion 12B and the diagnosis support information generated at step S4 in FIG. 2A is displayed on the display device 13.

For example, if judging that the legion candidate area included in the white light observation image in the display image D1 is flat and minute by confirming the diagnosis support information in the display image D1, the user decides a treatment policy for the legion candidate area based on the diagnosis support information. For example, if desiring to improve the degree of confidence in diagnosis for the legion candidate area included in the white light observation image in the display image D1 by confirming the diagnosis support information in the display image D1, the user gives an instruction to set the observation mode of the endoscope system 1 to the special light observation by operating the observation mode setting switch of the operation switch portion 11B. Further, the user sets a magnification MR for electronic magnification changing processing performed in the body device 12, by operating the electronic zoom switch of the operation switch portion 11B in a state in which the observation mode of the endoscope system 1 is set to the special light observation according to the diagnosis support information in the display image D1.

When detecting that the instruction to set the observation mode of the endoscope system 1 to the special light observation has been given by the observation mode setting switch of the operation switch portion 11B, the controlling portion 12C controls the light source portion 12A to generate special light including narrowband blue light and narrowband green light. Further, the controlling portion 12C controls the image processing portion 12B to perform magnification changing processing with the magnification MR. Then, in response to such control of the controlling portion 12C, the special light is supplied from the light source portion 12A to the endoscope 11; an image of return light from the object illuminated by the special light is picked up by the image pickup portion 11A; a special light observation image corresponding to an image pickup signal outputted from the image pickup portion 11A is generated by the image processing portion 12B; and an image obtained by performing magnification changing processing with the magnification MR for the special light observation image is displayed on the display device 13 as a display image and recorded to the image recording portion 21.

For example, by analyzing whether a character string showing the magnification MR, which is included in the special light observation image recorded to the image recording portion 21, exceeds a predetermined magnification (for example, a magnification of 1×) or not, the analysis processing portion 23A acquires an analysis result about whether the special light observation image is an enlarged image or not (step S5 in FIG. 2A). In other words, by analyzing the special light observation image recorded to the image recording portion 21, the analysis processing portion 23A acquires the analysis result about whether the special light observation image is an enlarged image or not, at step S5 in FIG. 2A.

If an analysis result that the special light observation image recorded to the image recording portion 21 is not an enlarged image is obtained by step S5 in FIG. 2A (S5: NO), the support item setting portion 23B sets likelihood of each class in a classification method available under unenlarged observation and the special light observation, which is an item corresponding to "special light observation+unenlarged" in the table TA, as a support item corresponding to the analysis results obtained by steps S1 and S5 in FIG. 2A, by referring to the table TA illustrated in FIG. 3 (step S6 in FIG. 2A). In other words, if an analysis result showing that the object in the subject is being observed by narrowband light observation and the analysis result showing that the special light observation image recorded to the image recording portion 21 is an unenlarged image are obtained, the support item setting portion 23B sets likelihood of each class by a classification method having a plurality of classes for classifying the legion candidate area according to a combination of the color tone and texture of the legion candidate area included in the special light observation image, as a support item at step S6 in FIG. 2A.

Note that, in the description related to FIGS. 2A, 2B and 3, the description will be made on a case where NICE (NBI international colorectal endoscopic) classification is used as a classification method available under the unenlarged observation and the special light observation, as an example. Therefore, according to the present embodiment, likelihood of each class in a different classification method other than the NICE classification may be set as a support item when the processing of step S6 in FIG. 2A is performed.

The support information generating portion 23C acquires an index corresponding to the support item set at step S6 in FIG. 2A, by referring to the diagnosis index information 22B stored in the storing portion 22.

More specifically, the support information generating portion 23C acquires, for example, as an index corresponding to the likelihood of each class, which is set by step S6 in FIG. 2A, in the classification method available under the unenlarged observation and the special light observation included in the support item, a classification index for classifying the legion candidate area included in the special light observation image using the plurality of classes in the classification method, by referring to the diagnosis index information 22B stored in the storing portion 22.

The support information generating portion 23C calculates, based on the index acquired according to the support item set at step S6 in FIG. 2A and the color tone and texture of the legion candidate area included in the same special light observation image that has been targeted by the processing of step S5 in FIG. 2A, the likelihood of each class in the case where the legion candidate area is classified using the plurality of classes in the classification method available under the unenlarged observation and the special light observation. Further, for example, by referring to a class with the highest likelihood among the likelihoods of the respective classes calculated as described above, the support information generating portion 23C acquires a judgment result about which of classes of tumor and non-tumor in the classification method the legion candidate area included in the special light observation image targeted by the processing of step S5 in FIG. 2A is classified into (step S7 in FIG. 2A).

If a judgment result that the legion candidate area included in the special light observation image targeted by the processing of step S5 in FIG. 2A is classified into the non-tumor class is obtained by step S6 in FIG. 2A (S7: NO), the support item setting portion 23B maintains the support item currently set (set by step S6 in FIG. 2A).

If obtaining the judgment result that the legion candidate area included in the special light observation image targeted by the processing of step S5 in FIG. 2A is classified into the non-tumor class, the support information generating portion 23C generates diagnosis support information including information about the likelihood of each class in the classification method available under the unenlarged observation and the special light observation calculated as described above and outputs the generated diagnosis support information to the body device 12 (step S8 in FIG. 2A).

The controlling portion 12C controls the image processing portion 12B to add the diagnosis support information outputted from the diagnosis support apparatus 2 to the special light observation image. According to such an operation of the controlling portion 12C, a display image D2 including the special light observation image generated by the image processing portion 12B and the diagnosis support information generated at step S8 in FIG. 2A is displayed on the display device 13.

If a judgment result that the legion candidate area included in the special light observation image targeted by the processing of step S5 in FIG. 2A is classified into the tumor class is obtained by step S7 in FIG. 2A (S7: YES), the support item setting portion 23B adds an inter-class area ratio, which is an item corresponding to "special light observation+unenlarged+tumor" in the table TA, to the support item set at step S6 in FIG. 2A, by referring to the table TA illustrated in FIG. 3 (step S9 in FIG. 2B). In other words, if the legion candidate area included in the special light observation image targeted by the processing of step S5 in FIG. 2A is classified into the tumor class, the support item setting portion 23B further sets the inter-class area ratio as a support item at step S9 in FIG. 2B.

If obtaining the judgment result that the legion candidate area included in the special light observation image targeted by the processing of step S5 in FIG. 2A is classified into the tumor class, the support information generating portion 23C calculates an inter-class area ratio in the case where the legion candidate area is classified using the plurality of classes, based on the support item added by step S9 in FIG. 2B and the color tone and texture of the legion candidate area. Then, the support information generating portion 23C generates diagnosis support information including the information showing the likelihood of each class in the classification method available under the unenlarged observation and the special light observation calculated as described above and information showing the inter-class area ratio calculated as described above, and outputs the generated diagnosis support information to the body device 12 (step S10 in FIG. 2B).

The controlling portion 12C controls the image processing portion 12B to add the diagnosis support information outputted from the diagnosis support apparatus 2 to the special light observation image. According to such an operation of the controlling portion 12C, a display image D3 including the special light observation image generated by the image processing portion 12B and the diagnosis support information generated at step S10 in FIG. 2B is displayed on the display device 13.

If an analysis result that the special light observation image recorded to the image recording portion 21 is an enlarged image is obtained by step S5 in FIG. 2A (S5: YES), the support item setting portion 23B sets likelihood of each class in a classification method available under the enlarged observation and the special light observation, which is an item corresponding to "special light observation+enlarged" in the table TA, as a support item corresponding to the analysis results obtained by steps S1 and S5 in FIG. 2A, by referring to the table TA illustrated in FIG. 3 (step S11 in FIG. 2A). In other words, if an analysis result showing that the object in the subject is being observed by the narrowband light observation and the analysis result showing that the special light observation image recorded to the image recording portion 21 is an enlarged image are obtained, the support item setting portion 23B sets likelihood of each class by a classification method having a plurality of classes for classifying the legion candidate area according to the texture of the legion candidate area included in the special light observation image, as a support item at step S11 in FIG. 2A.

Note that, in the description related to FIGS. 2A, 2B and 3, the description will be made on a case where JNET (The Japan NBI Expert Team) classification is used as a classification method available under the enlarged observation and the special light observation, as an example. Therefore, according to the present embodiment, likelihood of each class in a different classification method other than the JNET classification may be set as a support item when the processing of step S11 in FIG. 2A is performed.

The support information generating portion 23C acquires an index corresponding to the support item set at step S11 in FIG. 2A, by referring to the diagnosis index information 22B stored in the storing portion 22.

More specifically, the support information generating portion 23C acquires, for example, as an index corresponding to the likelihood of each class, which is set by Step S11 in FIG. 2A, in the classification method available under the enlarged observation and the special light observation included in the support item, a classification index for classifying the legion candidate area included in the special light observation image using the plurality of classes, by referring to the diagnosis index information 22B stored in the storing portion 22.

The support information generating portion 23C calculates, based on the index acquired according to the support item set at step S11 in FIG. 2A and the texture of the legion candidate area included in the same special light observation image that has been targeted by the processing of step S5 in FIG. 2A, the likelihood of each class in the case where the legion candidate area is classified using the plurality of classes in the classification method available under the enlarged observation and the special light observation. Further, for example, by referring to a class with the highest likelihood among the likelihoods of the respective classes calculated as described above, the support information generating portion 23C acquires a judgment result about which of classes of tumor and non-tumor the legion candidate area included in the special light observation image targeted by the processing of step S5 in FIG. 2A is classified into (step S12 in FIG. 2A).

If a judgment result that the legion candidate area included in the special light observation image targeted by the processing of step S5 in FIG. 2A is classified into the non-tumor class is obtained by step S12 in FIG. 2A (S12: NO), the support item setting portion 23B maintains the support item currently set (set by step S11 in FIG. 2A).

If obtaining the judgment result that the legion candidate area included in the special light observation image targeted by the processing of step S5 in FIG. 2A is classified into the non-tumor class, the support information generating portion 23C generates diagnosis support information including information about the likelihood of each class in the classification method available under the enlarged observation and the special light observation calculated as described above and outputs the generated diagnosis support information to the body device 12 (step S13 in FIG. 2A).

The controlling portion 12C controls the image processing portion 12B to add the diagnosis support information outputted from the diagnosis support apparatus 2 to the special light observation image. According to such an operation of the controlling portion 12C, a display image D4 including the special light observation image generated by the image processing portion 12B and the diagnosis support information generated at step S13 in FIG. 2A is displayed on the display device 13.

If a judgment result that the legion candidate area included in the special light observation image targeted by the processing of step S5 in FIG. 2A is classified into the tumor class is obtained by step S12 in FIG. 2A (S12: YES), the support item setting portion 23B adds an inter-class area ratio, which is an item corresponding to "special light observation+enlarged+tumor" in the table TA, to the support item set at step S11 in FIG. 2A, by referring to the table TA illustrated in FIG. 3 (set by step S14 in FIG. 2B). In other words, if the legion candidate area included in the special light observation image targeted by the processing of step S5 in FIG. 2A is classified into the tumor class, the support item setting portion 23B further sets the inter-class area ratio as a support item, at step S14 in FIG. 2B.

If obtaining the judgment result that the legion candidate area included in the special light observation image targeted by the processing of step S5 in FIG. 2A is classified into the tumor class, the support information generating portion 23C calculates an inter-class area ratio in the case where the legion candidate area is classified using the plurality of classes, based on the support item added by step S14 in FIG. 2B and the texture of the legion candidate area. Then, the support information generating portion 23C generates diagnosis support information including the information showing the likelihood of each class in the classification method available under the enlarged observation and the special light observation calculated as described above and information showing the inter-class area ratio calculated as described above, and outputs the generated diagnosis support information to the body device 12 (step S15 in FIG. 2B).

The controlling portion 12C controls the image processing portion 12B to add the diagnosis support information outputted from the diagnosis support apparatus 2 to the special light observation image. According to such an operation of the controlling portion 12C, a display image D5 including the special light observation image generated by the image processing portion 12B and the diagnosis support information generated at step S15 in FIG. 2B is displayed on the display device 13.

If, by confirming the diagnosis support information included in a display image DX corresponding to one of the display images D2 and D4, judging that the legion candidate area included in the special light observation image on the display image DX is either non-tumor or tumor, the user decides a treatment policy for the legion candidate area based on the diagnosis support information. If, by confirming the diagnosis support information included in the display image D5, judging that the legion candidate image on the display image D5 is any of adenoma, low severity degree and high severity degree, the user decides a treatment policy for the legion candidate area based on the diagnosis support information.

If an analysis result that the dye observation is being performed in the endoscope system 1 is obtained by step S2 in FIG. 2A (S2: YES), the support item setting portion 23B sets likelihood of each class in pit pattern classification, which is an item corresponding to "white light observation+ dye spraying" in the table TA, as a support item corresponding to the analysis results obtained by steps S1 and S2 in FIG. 2A, by referring to the table TA illustrated in FIG. 3 (step S16 in FIG. 2B). In other words, if an analysis result showing that the object in the subject is being observed by the white light observation and the analysis result showing that the legion candidate area included in the white light observation image is dyed are obtained, the support item setting portion 23B sets the likelihood of each class in the classification method having a plurality of classes for, according to the texture of the legion candidate area, classifying the legion candidate area, as a support item at step S16 in FIG. 2B.

The support information generating portion 23C acquires an index corresponding to the support item set at step S16 in FIG. 2B, by referring to the diagnosis index information 22B stored in the storing portion 22.

More specifically, the support information generating portion 23C acquires, for example, as an index corresponding to the likelihood of each class, which is set by step S16 in FIG. 2B, in the pit pattern classification included in the support item, a classification index for classifying the legion candidate area included in the white light observation image obtained during the dye observation, using the plurality of classes of the pit pattern classification, by referring to the diagnosis index information 22B stored in the storing portion 22.

The support information generating portion 23C calculates, based on the index acquired according to the support item set at step S16 in FIG. 2B and the texture of the legion candidate area included in the same white light observation image that has been targeted by the processing of step S2 in FIG. 2A, the likelihood of each class in the case where the legion candidate area is classified using the plurality of classes of the pit pattern classification. Then, the support information generating portion 23C generates diagnosis support information including the information showing the likelihood of each class in the pit pattern classification calculated as described above, and outputs the generated diagnosis support information to the body device 12 (step S17 in FIG. 2B).

The controlling portion 12C controls the image processing portion 12B to add the diagnosis support information outputted from the diagnosis support apparatus 2 to the white light observation image. According to such an operation of the controlling portion 12C, a display image D6 including the white light observation image generated by the image processing portion 12B and the diagnosis support information generated at step S17 in FIG. 2B is displayed on the display device 13.

By continuing the diagnosis support information included in the display image D6, the user decides a treatment policy for the legion candidate area according to whether the legion candidate area included in the white light observation image on the display image D6 infiltrates in submucosae or not.

In other words, according to the operation of each portion as described above, it is possible to, according to change of an observation state during observation of a legion candidate area discovered in a large intestine, automatically change (switch) a support item included in diagnosis support information for supporting diagnosis of the legion candidate area.

Figure 4:
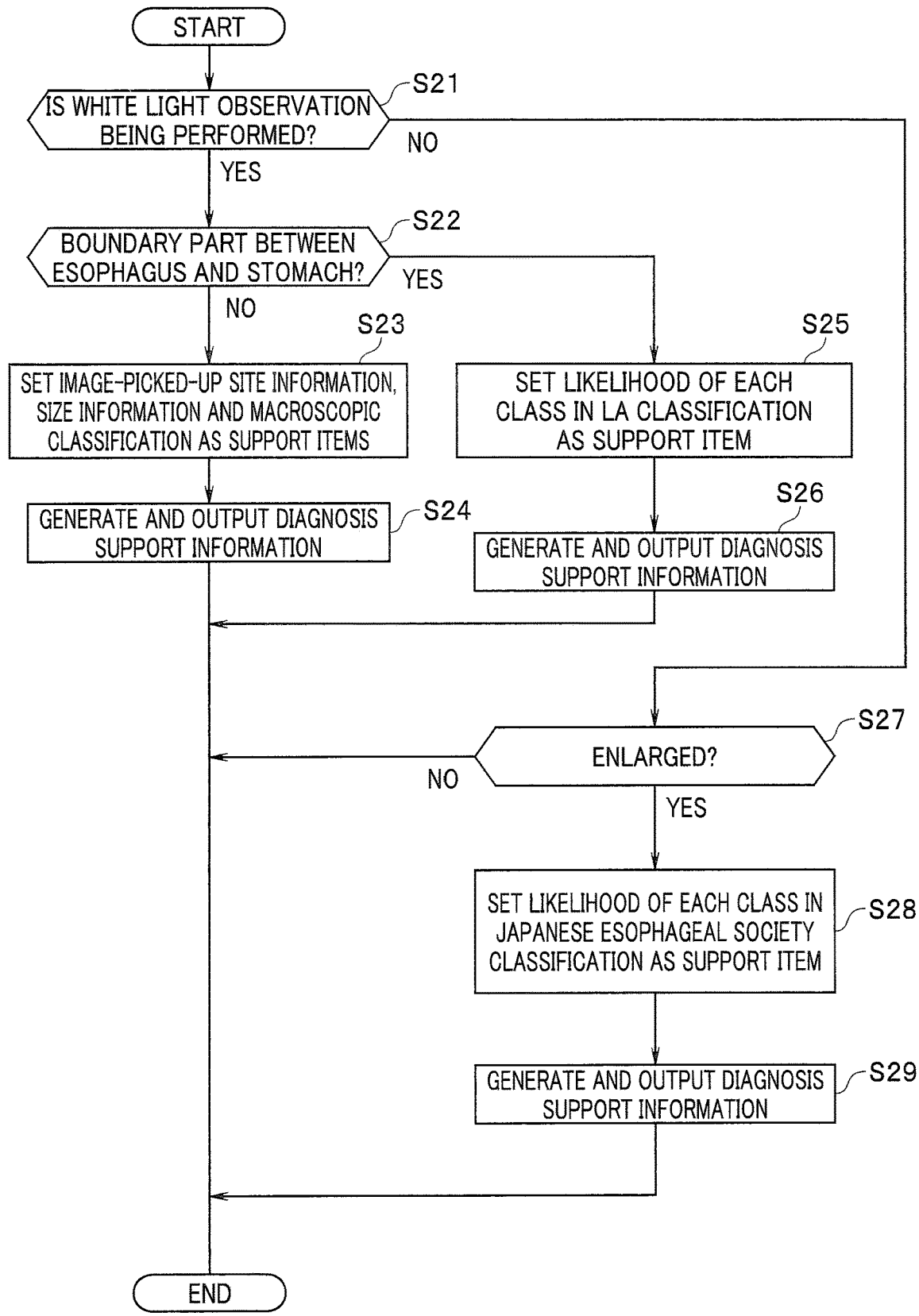
FIG. 4 is a flowchart showing a specific example of the process performed in the diagnosis support apparatus according to the embodiment.
Figure 5:
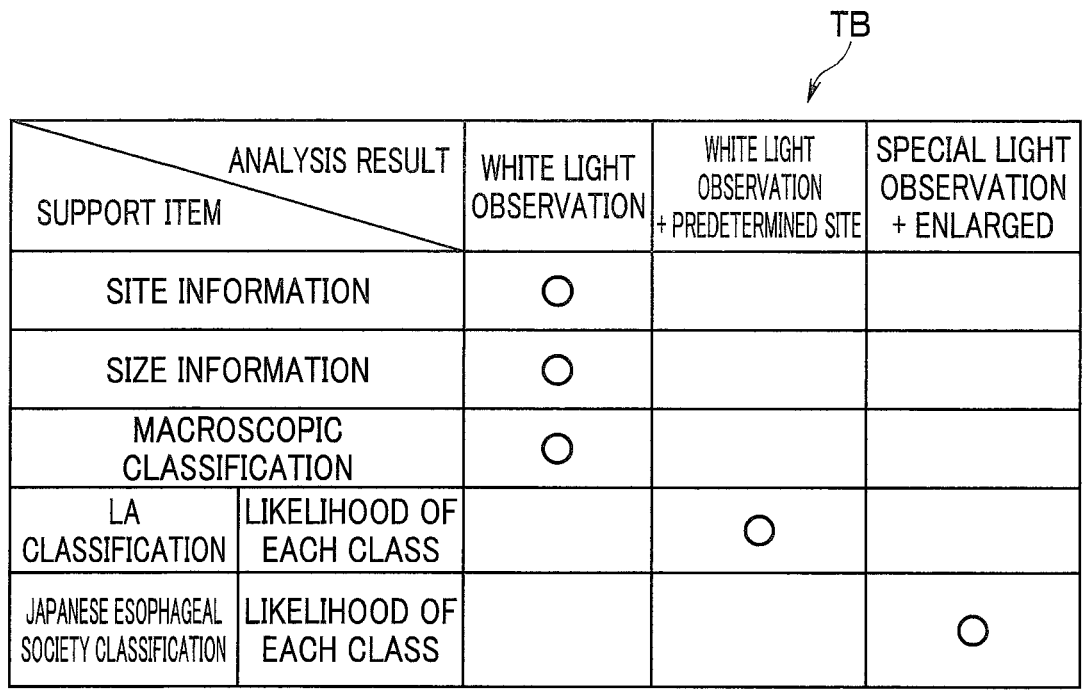
FIG. 5 is a diagram showing an example of a table referred to when the process shown in FIG. 4 is performed.

Note that, according to the present embodiment, for example, an operation for generating diagnosis support information usable for diagnosis of a legion candidate area discovered in an esophagus may be performed by each portion of the diagnosis support apparatus 2. A specific example of such a case will be described with reference to FIGS. 4 and 5. Hereinafter, specific description of a part to which a component or the like that has been already described is applicable will be appropriately omitted. FIG. 4 is a flowchart showing a specific example of the process performed in the diagnosis support apparatus according to the embodiment. FIG. 5 is a diagram showing an example of a table referred to when the process shown in FIG. 4 is performed.

After connecting each portion of the endoscope system 1 and turning on the power source, the user gives an instruction to set the observation mode of the endoscope system 1 to the white light observation by operating the observation mode setting switch of the operation switch portion 11B. After inserting the insertion portion of the endoscope 11 into the esophagus of an examinee, the user searches for a legion candidate area in the esophagus by confirming a white light observation image displayed on the display device 13. Then, when a legion candidate area is discovered by the user, a white light observation image including the legion candidate area is generated by the image processing portion 12B, and the white light observation image is displayed on the display device 13 as a display image and recorded to the image recording portion 21.

By analyzing the color tone and the like of the observation image recorded to the image recording portion 21, the analysis processing portion 23A acquires an analysis result about whether or not the white light observation is being performed in the endoscope system 1 (step S21 in FIG. 4). In other words, at step S21 in FIG. 4, by analyzing the color tone and the like of the observation image recorded to the image recording portion 21, the analysis processing portion 23A acquires an analysis result about which of the white light observation and the narrowband light observation the object in the subject is being observed by.

If obtaining an analysis result that the white light observation is being performed in the endoscope system 1 (S21: YES), the analysis processing portion 23A acquires image-picked-up site information, which is information showing a site in the subject where the legion candidate area included in the white light observation image has been image-picked up, based on the white light observation image recorded to the image recording portion 21, and stores the acquired image-picked-up site information into the storing portion 22. Further, if obtaining an analysis result that the white light observation is not being performed in the endoscope system 1, that is, an analysis result that the special light observation is being performed in the endoscope system 1 (S21: NO), the analysis processing portion 23A subsequently performs processing of step S27 in FIG. 4 described later.

If obtaining an analysis result that the white light observation is being performed in the endoscope system 1 (S21: YES), the analysis processing portion 23A acquires an analysis result about whether a boundary part between the esophagus and the stomach is included as an object in the white light observation image, by furthermore analyzing the color tone and the like of the same white light observation image that has been targeted by the processing of step S21 in FIG. 4 (step S22 in FIG. 4).

If the analysis result that the white light observation is being performed in the endoscope system 1 is obtained by step S21 in FIG. 4 (S21: YES), the support item setting portion 23B sets a support item, referring to, for example, a table TB as shown in FIG. 5, the table TB corresponding to the image-picked-up site information (esophagus) obtained together with the analysis result, in the support item correspondence information 22A stored in the storing portion 22. Note that the table TB may be configured having a format different from the format as shown in FIG. 5 as far as the table TB shows correspondence relationships between the analysis results of the observation image by the analysis processing portion 23A and the support item set by the support item setting portion 23B to support diagnosis of the legion candidate area discovered in the esophagus. It is assumed that, for example, until the image-picked-up site information stored in the storing portion 22 is updated from "esophagus" to a different site, the support item setting portion 23B sets a support item, referring to the table TB irrespective of whether the white light observation is being performed in the endoscope system 1 or not.

If an analysis result that the boundary part between the esophagus and the stomach is included as an object in the white light observation image is obtained by step S22 in FIG. 4 (S22: YES), the support item setting portion 23B subsequently performs processing of step S25 in FIG. 4 described later. If an analysis result that the boundary part between the esophagus and the stomach is not included in the white light observation image as an object is obtained by step S22 in FIG. 4 (S22: NO), the support item setting portion 23B sets each of image-picked-up site information, size information and macroscopic classification, which are items corresponding to "white light observation" in the table TB, as a support item corresponding to the analysis results obtained by steps S21 and S22 in FIG. 4, by referring to the table TB illustrated in FIG. 5 (step S23 in FIG. 4). In other words, if an analysis result showing that the object in the subject is being observed by the white light observation is obtained at step S23 in FIG. 4, the support item setting portion 23B sets each of a site in the subject where the legion candidate area has been image-picked up, the size of the legion candidate area, and a classification result by the macroscopic classification, which is a classification method having a plurality of classes for classifying the legion candidate area according to the shape of the legion candidate area, as a support item. Note that, according to the present embodiment, at step S23 in FIG. 4, at least one item has to be set as a support item among the site in the subject where the legion candidate area has been image-picked up, the size of the legion candidate area, and the classification result by the classification method having the plurality of classes for classifying the legion candidate area according to the shape of the legion candidate area.

The support information generating portion 23C acquires an index corresponding to the support items set at step S23 in FIG. 4, by referring to the diagnosis index information 22B stored in the storing portion 22.

More specifically, the support information generating portion 23C acquires, for example, as an index corresponding to the image-picked-up site information included among the support items set at step S23 in FIG. 4, an index for identifying the site in the subject where the legion candidate area has been image-picked up, based on one or more feature values and the like obtained from the white light observation image, by referring to the diagnosis index information 22B stored in the storing portion 22. Further, the support information generating portion 23C acquires, for example, as an index corresponding to the size information included among the support items set at step S23 in FIG. 4, an index for estimating the actual size of the legion candidate area included in the white light observation image, by referring to the diagnosis index information 22B stored in the storing portion 22. Further, the support information generating portion 23C acquires, for example, as an index corresponding to the macroscopic classification included among the support items set at step S23 in FIG. 4, a classification index for classifying the legion candidate area included in the white light observation image obtained by image-picking up the inside of the esophagus to any one of the plurality of classes in the macroscopic classification, by referring to the diagnosis index information 22B stored in the storing portion 22.

The support information generating portion 23C generates diagnosis support information based on the indexes acquired according to the support items set at step S23 in FIG. 4 and the same white light observation image that has been targeted by the processing of step S21 in FIG. 4, and outputs the generated diagnosis support information to the body device 12 (step S24 in FIG. 4). According to such an operation of step S24 in FIG. 4, for example, diagnosis support information including information showing that the legion candidate area discovered by the user exists in the esophagus, information showing a result of estimation of the actual length of the longest diameter of the legion candidate area, and information showing a classification result obtained by classifying the legion candidate area by the macroscopic classification is generated, and the generated diagnosis support information is outputted from the diagnosis support apparatus 2 to the body device 12.

Note that, when generating the diagnosis support information at step S24 in FIG. 4, the support information generating portion 23C may use the image-picked-up site information obtained together with the analysis result by step S21 in FIG. 4.

The support item setting portion 23B sets likelihood of each class in a method of classification according to the degree of inflammation, which is an item corresponding to "white light observation+predetermined site" in the table TB as a support item corresponding to the analysis results obtained by steps S21 and S22 in FIG. 4, by referring to the table TB illustrated in FIG. 5 (S25 in FIG. 4).

Note that, in the description related to FIGS. 4 and 5, the description will be made on a case where LA (Los Angeles) classification is used as the method of classification according to the degree of inflammation, as an example. Therefore, according to the present embodiment, likelihood of each class in a different classification method other than the LA classification may be set as a support item when the processing of step S25 in FIG. 4 is performed.

The support information generating portion 23C acquires an index corresponding to the support item set at step S25 in FIG. 4, by referring to the diagnosis index information 22B stored in the storing portion 22.

More specifically, the support information generating portion 23C acquires, for example, as an index corresponding to the likelihood of each class, which is set by step S25 in FIG. 4, in the method of classification according to the degree of inflammation included in the support item, a classification index for classifying the legion candidate area included in the white light observation image using the plurality of classes in the classification method, by referring to the diagnosis index information 22B stored in the storing portion 22.

The support information generating portion 23C calculates, based on the index acquired according to the support item set at step S25 in FIG. 4 and the texture of the legion candidate area included in the same white light observation image that has been targeted by the processing of step S22 in FIG. 4, the likelihood of each class in the case where the legion candidate area is classified using the plurality of classes in the method of classification according to the degree of inflammation. The support information generating portion 23C generates diagnosis support information including the information showing the likelihood of each class calculated as described above, and outputs the generated diagnosis support information to the body device 12 (step S26 in FIG. 4).

By operating the operation switch portion 11B while confirming the diagnosis support information of a display image displayed on the display device 13, the user gives an instruction for setting the observation mode of the endoscope system 1 to the special light observation and/or sets a magnification MS for the electronic magnification changing processing performed in the body device 12.

For example, by analyzing whether a character string showing the magnification MS, which is included in the special light observation image recorded to the image recording portion 21, exceeds a predetermined magnification (for example, a magnification of 1×) or not, the analysis processing portion 23A acquires an analysis result about whether the special light observation image is an enlarged image or not (step S27 in FIG. 4). In other words, by analyzing the special light observation image recorded to the image recording portion 21, the analysis processing portion 23A acquires the analysis result about whether the special light observation image is an enlarged image or not, at step S27 in FIG. 4.

If an analysis result that the special observation image recorded to the image recording portion 21 is an unenlarged image is obtained by step S27 in FIG. 4 (S27: NO), the support item setting portion 23B ends the process without setting a support item.

Note that, in the present embodiment, if the analysis result that the special observation image recorded to the image recording portion 21 is an unenlarged image is obtained by step S27 in FIG. 4, for example, information usable for diagnosis of a range of cancer in an esophagus may be set as a support item.

If an analysis result that the special light observation image recorded to the image recording portion 21 is an enlarged image is obtained by step S27 in FIG. 4 (S27: YES), the support item setting portion 23B sets likelihood of each class in a classification method related to classification of superficial cancer, which is an item corresponding to "special light observation+enlarged" in the table TB, as a support item corresponding to the analysis results obtained by steps S21 and S27 in FIG. 4, by referring to the table TB illustrated in FIG. 5 (step S28 in FIG. 4). In other words, if an analysis result showing that the object in the subject is being observed by the narrowband light observation and the analysis result showing that the special light observation image recorded to the image recording portion 21 is an enlarged image are obtained, the support item setting portion 23B sets the likelihood of each class by the classification method having the plurality of classes for classifying the legion candidate area according to the texture of the legion candidate area included in the special light observation image, as a support item at step S28 in FIG. 4.

Note that, in the description related to FIGS. 4 and 5, the description will be made on a case where Japanese Esophageal Society Classification is used as the classification method related to classification of superficial cancer, as an example. Therefore, according to the present embodiment, likelihood of each class in a different classification method other than Japanese Esophageal Society Classification (for example, Inoue's classification or Arima's classification) may be set as a support item when the processing of step S25 in FIG. 4 is performed.

The support information generating portion 23C acquires an index corresponding to the support item set at step S28 in FIG. 4, by referring to the diagnosis index information 22B stored in the storing portion 22.

More specifically, the support information generating portion 23C acquires, for example, as an index corresponding to the likelihood of each class, which is set by step S28 in FIG. 4, in the classification method related to classification of superficial cancer included in the support item, a classification index for classifying the legion candidate area included in the special light observation image using the plurality of classes in the classification method, by referring to the diagnosis index information 22B stored in the storing portion 22.

The support information generating portion 23C calculates, based on the index acquired according to the support item set at step S28 in FIG. 4 and the texture of the legion candidate area included in the same special light observation image that has been targeted by the processing of step S27 in FIG. 4, the likelihood of each class in the case where the legion candidate area is classified using the plurality of classes in the classification method related to classification of superficial cancer. The support information generating portion 23C generates diagnosis support information including the information showing the likelihood of each class calculated as described above, and outputs the generated diagnosis support information to the body device 12 (step S29 in FIG. 4).

In other words, according to the operation of each portion as described above, it is possible to, according to change of an observation state during observation of a legion candidate area discovered in an esophagus, automatically change (switch) a support item included in diagnosis support information for supporting diagnosis of the legion candidate area.

Figure 6:
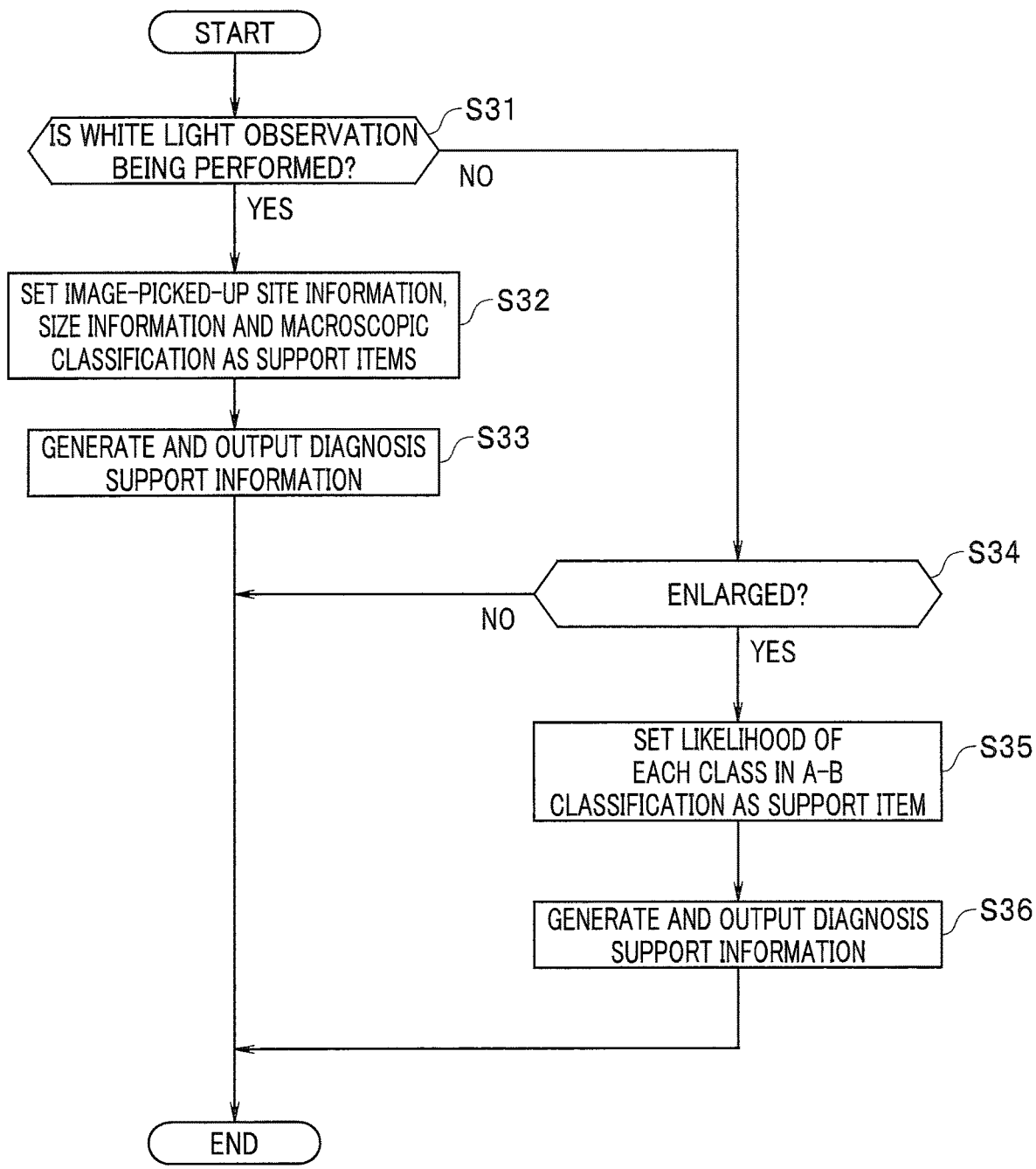
FIG. 6 is a flowchart showing a specific example of the process performed in the diagnosis support apparatus according to the embodiment.
Figure 7:
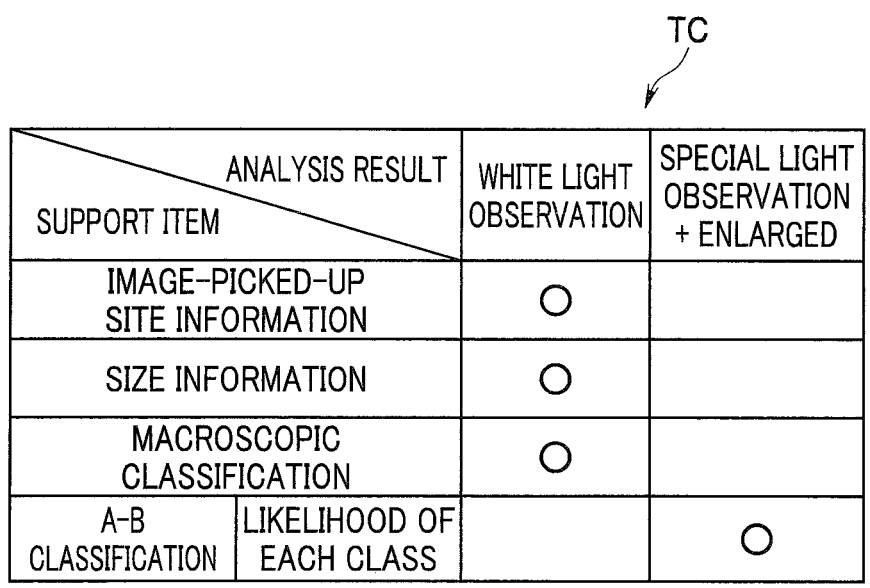
FIG. 7 is a diagram showing an example of a table referred to when the process shown in FIG. 6 is performed.

Note that, according to the present embodiment, for example, an operation for generating diagnosis support information usable for diagnosis of a legion candidate area discovered in a stomach may be performed by each portion of the diagnosis support apparatus 2. A specific example of such a case will be described with reference to FIGS. 6 and 7. FIG. 6 is a flowchart showing a specific example of the process performed in the diagnosis support apparatus according to the embodiment. FIG. 7 is a diagram showing an example of a table referred to when the process shown in FIG. 6 is performed.

After connecting each portion of the endoscope system 1 and turning on the power source, the user gives an instruction to set the observation mode of the endoscope system 1 to the white light observation by operating the observation mode setting switch of the operation switch portion 11B. After inserting the insertion portion of the endoscope 11 into the stomach of an examinee, the user searches for a legion candidate area in the stomach by confirming a white light observation image displayed on the display device 13. Then, when a legion candidate area is discovered by the user, a white light observation image including the legion candidate area is generated by the image processing portion 12B, and the white light observation image is displayed on the display device 13 as a display image and recorded to the image recording portion 21.

By analyzing the color tone and the like of the observation image recorded to the image recording portion 21, the analysis processing portion 23A acquires an analysis result about whether or not the white light observation is being performed in the endoscope system 1 (step S31 in FIG. 6). In other words, at step S31 in FIG. 6, by analyzing the color tone and the like of the observation image recorded to the image recording portion 21, the analysis processing portion 23A acquires an analysis result about which of the white light observation and the narrowband light observation the object in the subject is being observed by.

If obtaining an analysis result that the white light observation is being performed in the endoscope system 1 (S31: YES), the analysis processing portion 23A acquires image-picked-up site information, which is information showing a site in the subject where the legion candidate area included in the white light observation image has been image-picked up, based on the white light observation image recorded to the image recording portion 21, and stores the acquired image-picked-up site information into the storing portion 22. Further, if obtaining an analysis result that the white light observation is not being performed in the endoscope system 1, that is, an analysis result that the special light observation is being performed in the endoscope system 1 (S31: NO), the analysis processing portion 23A subsequently performs processing of step S34 in FIG. 6 described later.

If the analysis result that the white light observation is being performed in the endoscope system 1 is obtained by step S31 in FIG. 6 (S31: YES), the support item setting portion 23B sets a support item, referring to, for example, a table TC as shown in FIG. 7, the table TC corresponding to image-picked-up site information (stomach) obtained together with the analysis result, in the support item correspondence information 22A stored in the storing portion 22. Note that the table TC may be configured having a format different from the format as shown in FIG. 7 as far as the table TC shows correspondence relationships between the analysis results of the observation image by the analysis processing portion 23A and the support item set by the support item setting portion 23B to support diagnosis of the legion candidate area discovered in the stomach. It is assumed that, for example, until the image-picked-up site information stored in the storing portion 22 is updated from "stomach" to a different site, the support item setting portion 23B sets a support item, referring to the table TC irrespective of whether the white light observation is being performed in the endoscope system 1 or not.

If the analysis result that the white light observation is being performed in the endoscope system 1 is obtained by step S31 in FIG. 6 (S31: YES), the support item setting portion 23B sets each of image-picked-up site information, size information and macroscopic classification, which are items corresponding to "white light observation" in the table TC as a support item corresponding to the analysis result obtained by step S31 in FIG. 6, by referring to the table TC illustrated in FIG. 7 (step S32 in FIG. 6). In other words, if an analysis result showing that the object in the subject is being observed by the white light observation is obtained at step S32 in FIG. 6, the support item setting portion 23B sets each of a site in the subject where the legion candidate area has been image-picked up, the size of the legion candidate area, and a classification result by macroscopic classification, which is a classification method having a plurality of classes for classifying the legion candidate area according to the shape of the legion candidate area, as a support item. Note that, according to the present embodiment, at step S32 in FIG. 6, at least one item has to be set as a support item among the site in the subject where the legion candidate area has been image-picked up, the size of the legion candidate area, and the classification result by the classification method having the plurality of classes for classifying the legion candidate area according to the shape of the legion candidate area.

The support information generating portion 23C acquires an index corresponding to the support items set at step S32 in FIG. 6, by referring to the diagnosis index information 22B stored in the storing portion 22.

More specifically, the support information generating portion 23C acquires, for example, as an index corresponding to the image-picked-up site information included among the support items set at step S32 in FIG. 6, an index for identifying the site in the subject where the legion candidate area has been image-picked up, based on one or more feature values and the like obtained from the white light observation image, by referring to the diagnosis index information 22B stored in the storing portion 22. Further, the support information generating portion 23C acquires, for example, as an index corresponding to the size information included among the support items set at step S32 in FIG. 6, an index for estimating the actual size of the legion candidate area included in the white light observation image, by referring to the diagnosis index information 22B stored in the storing portion 22. Further, the support information generating portion 23C acquires, for example, as an index corresponding to the macroscopic classification included among the support items set at step S32 in FIG. 6, a classification index for classifying the legion candidate area included in the white light observation image obtained by image-picking up the inside of the stomach to any one of the plurality of classes in the macroscopic classification, by referring to the diagnosis index information 22B stored in the storing portion 22.

The support information generating portion 23C generates diagnosis support information based on the indexes acquired according to the support items set at step S32 in FIG. 6 and the same white light observation image that has been targeted by the processing of step S31 in FIG. 6, and outputs the generated diagnosis support information to the body device 12 (step S33 in FIG. 6). According to such an operation of step S33 in FIG. 6, for example, diagnosis support information including information showing that the legion candidate area discovered by the user exists in the stomach, information showing a result of estimation of the actual length of the longest diameter of the legion candidate area, and information showing a classification result obtained by classifying the legion candidate area by the macroscopic classification is generated, and the generated diagnosis support information is outputted from the diagnosis support apparatus 2 to the body device 12.

Note that, when generating the diagnosis support information at step S33 in FIG. 6, the support information generating portion 23C may use the image-picked-up site information obtained together with the analysis result by step S21 in FIG. 6.

By operating the operation switch portion 11B while confirming the diagnosis support information of a display image displayed on the display device 13, the user gives an instruction for setting the observation mode of the endoscope system 1 to the special light observation and/or sets a magnification MT for the electronic magnification changing processing performed in the body device 12.

For example, by analyzing whether a character string showing the magnification MT, which is included in the special light observation image recorded to the image recording portion 21, exceeds a predetermined magnification (for example, a magnification of 1×) or not, the analysis processing portion 23A acquires an analysis result about whether the special light observation image is an enlarged image or not (step S34 in FIG. 6). In other words, by analyzing the special light observation image recorded to the image recording portion 21, the analysis processing portion 23A acquires the analysis result about whether the special light observation image is an enlarged image or not, at step S34 in FIG. 6.

If an analysis result that the special light observation image recorded to the image recording portion 21 is an unenlarged image is obtained by step S34 in FIG. 6 (S34: NO), the support item setting portion 23B ends the process without setting a support item.

Note that, in the present embodiment, if the analysis result that the special light observation image recorded to the image recording portion 21 is an unenlarged image is obtained by step S34 in FIG. 6, for example, information usable for diagnosis of a range of cancer in a stomach may be set as a support item.

If an analysis result that the special light observation image recorded to the image recording portion 21 is an enlarged image is obtained by step S34 in FIG. 6 (S34: YES), the support item setting portion 23B sets likelihood of each class in a method of classification according to the degree of atrophy of fundic gland, which is an item corresponding to "special light observation+enlarged" in the table TC, as a support item corresponding to the analysis results obtained by steps S31 and S34 in FIG. 6, by referring to the table TC illustrated in FIG. 7 (step S35 in FIG. 6). In other words, if an analysis result showing that the object in the subject is being observed by the narrowband light observation and the analysis result showing that the special light observation image recorded to the image recording portion 21 is an enlarged image are obtained, the support item setting portion 23B sets the likelihood of each class by the classification method having the plurality of classes for classifying the legion candidate area according to the texture of the legion candidate area included in the special light observation image, as a support item at step S35 in FIG. 6.

Note that, in the description related to FIGS. 6 and 7, the description will be made on a case where A-B classification is used as the method of classification according to the degree of atrophy of fundic gland, as an example. Therefore, according to the present embodiment, likelihood of each class in a different classification method other than the A-B classification may be set as a support item when the processing of step S35 in FIG. 6 is performed.

The support information generating portion 23C acquires an index corresponding to the support item set at step S35 in FIG. 6, by referring to the diagnosis index information 22B stored in the storing portion 22.

More specifically, the support information generating portion 23C acquires, for example, as an index corresponding to the likelihood of each class, which is set by step S35 in FIG. 6, in the method of classification according to the degree of atrophy of fundic gland included in the support item, a classification index for classifying the legion candidate area included in the special light observation image using the plurality of classes in the classification method, by referring to the diagnosis index information 22B stored in the storing portion 22.

The support information generating portion 23C calculates, based on the index acquired according to the support item set at step S35 in FIG. 6 and the texture of the legion candidate area included in the same special light observation image that has been targeted by the processing of step S34 in FIG. 6, the likelihood of each class in the case where the legion candidate area is classified using the plurality of classes in the method of classification according to the degree of atrophy of fundic gland. The support information generating portion 23C generates diagnosis support information including the information showing the likelihood of each class calculated as described above, and outputs the generated diagnosis support information to the body device 12 (step S36 in FIG. 6).

In other words, according to the operation of each portion as described above, it is possible to, according to change of an observation state during observation of a legion candidate area discovered in a stomach, automatically change (switch) a support item included in diagnosis support information for supporting diagnosis of the legion candidate area.

As described above, according to the present embodiment, it is possible to, according to change of an observation state during endoscopic observation being actually performed, automatically change (switch) a support item included in diagnosis support information for supporting diagnosis of a legion candidate area discovered by the endoscopic observation. Therefore, according to the present embodiment, it is possible to reduce the burden on the user during endoscopic observation.

Note that, according to the present embodiment, the analysis processing portion 23A is not limited to obtaining image-picked-up site information by analyzing a white light observation image (recorded to the image recording portion 21) outputted from the body device 12 but may obtain image-picked-up site information by analyzing an inserted shape image outputted from an inserted shape detection device configured to detect an inserted shape of the insertion portion of the endoscope 11 inserted in a subject and image the inserted shape.

Further, according to the present embodiment, the analysis processing portion 23A may obtain image-picked-up site information in which each part in a large intestine is subdivided, by analyzing a white light observation image recorded to the image recording portion 21 or an inserted shape image outputted from the inserted shape detection device. More specifically, the analysis processing portion 23A may obtain information showing that a legion candidate area has been image-picked up, for example, at any of sites of a rectum, a sigmoid colon, a descending colon, a traverse colon and an ascending colon as the image-picked-up site information by analyzing the white light observation image recorded to the image recording portion 21 or the inserted shape image outputted from the inserted shape detection device. Further, in the case of obtaining the image-picked-up site information as described above, the analysis processing portion 23A may count the number of legion candidate areas for each site in a large intestine and store the number into the storing portion 22.

Further, according to the present embodiment, for example, when the support item correspondence information 22A including a plurality of tables (for example, two or more tables among the tables TA, TB and TC) showing correspondence relationships between analysis results obtained by the analysis processing portion 23A and support items set by the support item setting portion 23B is stored in the storing portion 22, the support item setting portion 23B may select one table corresponding to a site in a subject (in a living body) where a legion candidate area included in an observation image has been image-picked up, among the plurality of tables, and set a support item.

Further, instead of such diagnosis support information that includes information showing likelihood of each class at a predetermined classification index being generated, for example, such diagnosis support information that includes information showing the largest value of likelihood obtained at the time of having classified a legion candidate area using the predetermined classification index and information showing a class for which the value of the largest likelihood at the predetermined classification index may be generated by appropriately modifying the configuration of the diagnosis support apparatus 2 of the present embodiment.

Further, for example, such diagnosis support information that includes information that shows a treatment policy corresponding to a classification result (a class) at the time of having classified a legion candidate area using a predetermined classification index by appropriately modifying the configuration of the diagnosis support apparatus 2 of the present embodiment.

Further, by appropriately modifying the configuration of the medical system 101 of the present embodiment, for example, the diagnosis support apparatus 2 may be provided between the body device 12 and the display device 13; each portion of the diagnosis support apparatus 2 may be built in the body device 12; or a program constructed to perform processing corresponding to the function of each portion of the operating portion 23 may be executed by the controlling portion 12C.

Note that the present invention is not limited to the embodiment described above, and, of course, various changes and applications are possible within a range not departing from the gist of the invention.

What is claimed is:

1. A diagnosis support apparatus performing identification for a plurality of support items, which are identification classifications about diagnosis support, the diagnosis support apparatus comprising a processor, wherein the processor
performs analysis processing for acquiring analysis results including an analysis result about an observation mode by analyzing at least one of an input signal specifying the observation mode and an observation image obtained by observing an inside of a subject with an endoscope, the analysis results being related to an observation condition of the observation image;
performs support item setting processing for setting a support item corresponding to the analysis results obtained by the analysis processing, among the plurality of support items, which are the identification classifications; and
generates diagnosis support information, which is information related to the support item and is used for diagnosis of a legion candidate area included in the observation image, based on an identification index corresponding to the set support item and the observation image.

2. The diagnosis support apparatus according to claim 1, wherein the processor acquires an analysis result about which of white light observation and narrowband light observation an object in the subject is observed by, by analyzing either the observation image or an input signal inputted while observing the inside of the subject with the endoscope.

3. The diagnosis support apparatus according to claim 2, wherein if an analysis result showing that the object in the subject is observed by the white light observation is obtained, the processor sets at least one of a site in the subject where the legion candidate area has been image-picked up, a size of the legion candidate area and a classification result by a classification method having a plurality of classes for classifying the legion candidate area according to a shape of the legion candidate area, as the support item.

4. The diagnosis support apparatus according to claim 2, wherein if the analysis result that the object in the subject is observed by the white light observation is obtained, the processor further acquires an analysis result about whether the legion candidate area is dyed or not by analyzing the observation image; and
if the analysis result showing that the object in the subject is observed by the white light observation and an analysis result showing that the legion candidate area is dyed are obtained, the processor sets likelihood of each class in a classification method having a plurality of classes for classifying the legion candidate area according to texture of the legion candidate area, as the support item.

5. The diagnosis support apparatus according to claim 2, wherein if an analysis result that the object in the subject is observed by the narrowband light observation is obtained, the processor further acquires an analysis result about whether the observation image is an enlarged image or not by analyzing the observation image.

6. The diagnosis support apparatus according to claim 5, wherein if the analysis result showing that the object in the subject is observed by the narrowband light observation and an analysis result showing that the observation image is an enlarged image are obtained, the processor sets likelihood of each class in a classification method having a plurality of classes for classifying the legion candidate area according to the texture of the legion candidate area, as the support item.

7. The diagnosis support apparatus according to claim 6, wherein if the legion candidate area is classified as a tumor class in the classification method, the processor further sets an inter-class area ratio in the classification method as the support item.

8. The diagnosis support apparatus according to claim 5, wherein if the analysis result showing that the object in the subject is observed by the narrowband light observation and an analysis result showing that the observation image is an unenlarged image are obtained, the processor sets likelihood of each class in a classification method having a plurality of classes for classifying the legion candidate area according to a combination of a color tone and the texture of the legion candidate area, as the support item.

9. The diagnosis support apparatus according to claim 8, wherein if the legion candidate area is classified as a tumor class in the classification method, the processor further sets an inter-class area ratio in the classification method as the support item.

10. The diagnosis support apparatus according to claim 1, further comprising a storing portion in which a plurality of tables showing correspondence relationships between the analysis results obtained by the processor and the support items are stored, wherein the processor selects one table corresponding to a site in the subject where the legion candidate area has been image-picked up, among the plurality of tables, and sets the support item.

11. A diagnosis support method for performing identification for a plurality of support items, which are identification classifications about diagnosis support, the diagnosis support method comprising:

performing analysis processing for acquiring analysis results including an analysis result about an observation mode by analyzing at least one of an input signal specifying the observation mode and an observation image obtained by observing an inside of a subject with an endoscope, the analysis results being related to an observation condition of the observation image;

setting a support item corresponding to the analysis results obtained by the analysis processing, among the plurality of support items, which are the identification classifications; and generating diagnosis support information, which is information related to the support item and is used for diagnosis of a legion candidate area included in the observation image, based on an identification index corresponding to the set support item and the observation image.

12. A computer-readable non-transitory storage medium in which a program for performing identification for a plurality of support items which are identification classifications about diagnosis support is stored, wherein the program causes a computer to execute a procedure of:

acquiring analysis results including an analysis result about an observation mode by analyzing at least one of an input signal specifying the observation mode and an observation image obtained by observing an inside of a subject with an endoscope, the analysis results being related to an observation condition of the observation image;

setting a support item corresponding to the analysis results among the plurality of support items, which are the identification classifications; and generating diagnosis support information, which is information related to the support item and is used for diagnosis of a legion candidate area included in the observation image, based on an identification index corresponding to the set support item and the observation image.

\* \* \* \* \*